United States Patent [19]

Cregg et al.

[11] Patent Number: 4,929,555
[45] Date of Patent: May 29, 1990

[54] PICHIA TRANSFORMATION

[75] Inventors: James M. Cregg; Kevin J. Barringer, both of San Diego, Calif.

[73] Assignee: Phillips Petroleum Company, Bartlesville, Okla.

[21] Appl. No.: 110,148

[22] Filed: Oct. 19, 1987

[51] Int. Cl.$^5$ .................... C12N 15/00; C12N 5/00
[52] U.S. Cl. .................... 435/172.3; 435/255; 435/256; 435/320; 435/172.1; 935/55; 935/56; 935/69
[58] Field of Search ............ 435/68, 70, 172.1, 172.3, 435/255, 256, 320; 935/55, 56, 69

[56] References Cited

PUBLICATIONS

Cregg et al, Mol. Cell Biol., vol. 5, pp. 3376–3385, 1985.
J. Bact. Jan. 1983, pp. 163–168—"Transformation of Intact Yeast Cells Treated with Alkali Cations" by Hisao Ito et al.
Current Genetics (1985) 10:39–48—"Integrative Transformation of the Yeast Yarrowia lipolytica" by Lance S. Davidow et al.
Mol Gen. Genet (1986) 202:302–308—"Transformation of the Methylotrophic Yeast Hansenula polymorpha by Autonomous Replication and Integration Vectors" by Rainer Roggenkamp et al.
Molecular and Cellular Biol. Jan 1986, pp. 80–89—"Replicating Plasmids in Schizosaccharomyces pombe: Improvement of Symmetric Segregation by a New Genetic Element" by Wolf-Dietrich Heyer et al.
J. Basic Microbiol. 25 (1985) 2, 141–144—"Transformation of the Industrially Important Yeasts Candida maltosa and Pichia guilliermondii" by G. Kunze et al.
J. Bacteriology, Jun. 1984, pp. 1165–1167—"Transformation of Kluyveromyces fragilis" by Sunil Das et al.

Primary Examiner—Robin Lyn Teskin
Attorney, Agent, or Firm—J. E. Phillips

[57] ABSTRACT

The present invention provides a method for making whole cells of methylotrophic species of genus Pichia competent for transformation by DNA and a method for transforming with DNA whole cells of such species.

23 Claims, No Drawings

PICHIA TRANSFORMATION

TECHNICAL FIELD

The present invention relates to molecular biology and genetic engineering.

More particularly, in one aspect the invention relates to a method of making yeast cells from the genus Pichi competent for transformation by DNA foreign to the cells. In another aspect the invention relates to a method for transforming such cells with such DNA.

BACKGROUND OF THE INVENTION

An essential step in the genetic engineering of cells to carry out a desired function, such as production of a desired protein, is to transform the cells with a DNA, which includes the genetic information necessary for the cells to carry out the function. However, before cells can be transformed with a DNA, they must be treated to be made competent for transformation.

Transformation of yeast cells presents special problems because such cells have cell walls, in addition to plasma membranes, as barriers to entry of DNA.

One common method for transforming yeast cells is to first form spheroplasts from the cells by enzymatically digesting away the cell walls of the cells, then treating the spheroplasts to transform them with the desired DNA, and finally treating the transformed spheroplasts to regenerate the whole cells, complete with cell walls. A typical transformation process, employing spheroplasts of cells of the methylotrophic yeast species *Pichia pastoris*, is described by Cregg et al., Mol. Cell. Biol. 5, 3376–3385 (1985).

Employing spheroplasts for transformation of yeast cells entails a number of disadvantages associated with the osmotic sensitivity of spheroplasts and the need to first make spheroplasts and then reform whole cells from them. In recognition of these problems, efforts have been made in the art to devise methods for transforming whole yeast cells.

Thus, Ito et al., J. Bacteriol. 153, 163–168 (1983), have reported a method for making competent for transformation and transforming whole cells of *Saccharomyces cerevisiae*. The method of Ito et al. involves incubating whole cells of *Saccharmoyces cerevisiae* in an aqueous solution, buffered at a pH of about 8, of a salt of an alkali metal, to render the cells competent for transformation; incubating the competent, whole cells in a solution, again buffered to a pH of about 8, with the DNA with which the cells are to be transformed and a salt of an alkali metal; adding to the DNA solution bathing the cells polyethylene glycol, with an average molecular weight of about 4000, to bring the polyethylene glycol concentration to about 35% (w/v); incubating the cells in the resulting solution; and heat shocking the cells by suspending the solution in a water bath at 42° C. for five minutes and then returning the solution to room temperature. Among the salts of alkali metals tested by Ito et al., at 0.1 M concentration in both the solution for making the cells competent for transformation and the transforming solution (prior to addition of polyethylene glycol), lithium chloride resulted in four to eight times more transformants per microgram of transforming DNA than sodium chloride. Further, among the lithium salts tested lithium chloride yielded a significantly lower number of transformants per microgram of transforming DNA than lithium acetate, lithium nitrate and lithium sulfate, all of which yielded about the same number of transformants. Ito et al. reported that circular plasmid DNA transformed alkali metal salt-treated whole cells more efficiently than linearized plasmid DNA and that cells from mid- to late-log phase cultures, when treated with an alkali metal salt, were transformed more efficiently than cells from late-log to stationary phase cultures. Ito et al. reported maximum transformation efficiency when the ratio of the concentration of cells treated with the salt of an alkali metal to the concentration of the alkali metal salt was between about $10^{11}$ to about $10^{12}$ cells per mole.

Davidow et al., Curr. Genet. 10, 39–48 (1985), reported a method for making competent for transformation and transforming whole cells of the yeast *Yarrowia lipolytica*. The method of Davidow et al. involves incubating whole cells of *Yarrowia lipolytica* at about $10^8$ cells per ml in an aqueous solution, buffered at a pH of about 7.5 of 0.1 M lithium acetate to render the cells competent for transformation; incubating the competent, whole cells in a solution again buffered to a pH of about 7.5, of the DNA with which the cells are to be transformed, heterologous carrier DNA (*E. coli* DNA) HaeIII digested to a size range of less than 1 kilobase pair, and 0.1 M lithium acetate; adding to the DNA solution bathing the cells a solution of 0.1 M lithium acetate buffered to a pH of about 7.5 and containing about 40% (w/v) polyethylene glycol, with an average molecular weight of about 4000, to bring the polyethylene glycol concentration to about 35% (w/v) in the DNA-containing solution; incubating the resulting solution; and subjecting the cells in the polyethylene glycol solution to a heat shock by suspending the solution at 37° C. for several minutes. Contrary to Ito et al., Davidow et al. reported that circular plasmid DNA transformed lithium acetate-treated whole cells less efficiently than linearized plasmid DNA. Similar to Ito et al., Davidow et al found that cells from cultures in later stages of growth gave more transformants per microgram of transforming DNA than cells from cultures in early stages of growth. Davidow et al. reported that more than about 50 micrograms of the HaeIII digested carrier DNA per microgram of transforming DNA significantly increased the number of transformants obtained per microgram of transforming DNA; and sonicated *E. coli* DNA (size range 0.5–9 kbp) as carrier, present at 50 micrograms per microgram of transforming DNA, resulted in only half as many transformants per microgram of transforming DNA as HaeIII digested *E. coli* DNA (size range less than 1 kbp) as carrier also present at 50 micrograms per microgram of transforming DNA.

The differing results of Ito et al. and Davidow et al. illustrate the unpredictability of the effectiveness for any particular species of yeast of processes for making competent for transformation and transforming whole cells. In fact, whether methods found to be effective with one species of yeast will be effective with another species, on which the methods have not been tested, is highly uncertain. The properties of cell walls and associated membranes which affect competence for transformation and transformation efficiency remain obscure for all species and, particularly, species of yeast. It is thought that the chemical and physical properties of cell walls and membranes differ significantly among species of yeast, but how these differences might affect methods for making yeast competent for transformation or for transforming them, and the efficiency with which any particular method will function with a particular species, remain unknown.

The more distant taxonomically two species of yeast are, the less likely it is that observations concerning whole cell transformation methods made with one of the species will hold true for the other. In particular, nothing is known in the art about whole cell transformation methods applied to methylotrophic yeasts, such as those of the species *Pichia pastoris*. Methylotrophic yeasts differ significantly in numerous properties, including properties pertinent to processes for making cells competent for transformation and for transforming them, from non-methylotrophic yeasts such as *S. cerevisiae* and *Y. lipolytica*.

SUMMARY OF THE INVENTION

We have now discovered that whole cells of methylotrophic species of the genus Pichia can be made competent for transformation by incubation in a buffered solution of lithium chloride or lithium sulfate. We have found further, unexpectedly, that such cells made competent for transformation by such a process can be frozen and stored, in the frozen state, until use with little decrease in efficiency with which the cells can be transformed. Frozen storage is difficult with spheroplasts of such cells, so that the many practical advantages of such storage could not be realized for such cells prior to the present invention.

We have also discovered that whole cells of methylotrophic species of the genus Pichia, after being made competent for transformation by incubation in a buffered solution of lithium chloride or lithium solfonate, can be transformed with a desired DNA by incubation with a buffered solution of the DNA and lithium chloride or lithium sulfate, followed by addition to the solution to a concentration of between 20% (w/v) and about 50%, preferably about 35% (w/v), polyethylene glycol with an average molecular weight about between about 3000 and about 5000 daltons, preferably 3350 daltons and subsequent incubation of the polyethylene glycol-containing solution, and followed in turn by heat shocking the solution. We have found, further, unexpectedly that this transformation method has certain significant advantages over methods of transforming such cells which employ spheroplasts of the cells. In particular, the whole cell procedure yields transformants which, because they are not embedded in agar, grow significantly faster than transformants made using spheroplasts.

DETAILED DESCRIPTION OF THE INVENTION

The present invention entails a novel and unexpectedly advantageous method for making whole cells of a methylotrophic species of genus Pichia competent for transformation, said method comprising maintaining said cells in suspension for at least about 45 minutes at a concentration between about $5 \times 10^7$ and about $5 \times 10^8$, preferably about $1.25 \times 10^8$ cells/ml in an aqueous solution of lithium chloride or lithium sulfate at a concentration between about 50 mM and about 500 mM, said solution maintained at a temperature between about 27° C. and about 33° C. and buffered at a pH between about 7 and about 8, preferably about 7.

The invention entails further a novel and advantageous method for transforming whole cells of a methylotrophic species of genus Pichia with a desired DNA, which method comprises:

(1) providing cells of the species which have been made competent for transformation by a method comprising maintaining said cells in suspension for at least about 45 minutes at a concentration between about $5 \times 10^7$ and about $5 \times 10^8$ cells/ml in a first aqueous solution of lithium chloride or lithium sulfate at a concentration between about 50 mM and about 500 mM, said first solution maintained at a temperature between about 27° C. and about 33° C. and buffered at a pH between about 7 and about 8;

(2) making a second suspension of cells by combining (a) a first suspension of said competent cells, at a concentration between about $5 \times 10^7$ and about $5 \times 10^8$ cells/ml, in a second aqueous solution comprising a salt of lithium, which is the same as the first salt of lithium, at a concentration between about 50 mM and about 500 mM and buffered at a pH between about 6 and about 8, with (b) a third aqueous solution with a volume less than $0.2 \times$ that of said first suspension, said third solution buffered at a pH between about 7 and about 8 and comprising between about 1 ng and about 20 μg of said desired DNA per ml of said first suspension combined with said third solution, provided that, if said amount of said desired DNA is less than about 10 μg per ml of said first suspension combined with said third solution, said third solution comprises a mass of carrier DNA of 10 μg, provided further that the amounts of said desired DNA and said carrier DNA are such that the amount of said carrier DNA does not exceed 50 μg per ml of said first suspension combined with said third solution;

(3) incubating at least a portion of said second suspension made in step (2) at between about 27° C. and about 33° C. for at least about 10 minutes to 60 minutes, preferably about 30 minutes;

(4) making a third suspension of said cells by mixing, to establish substantially homogeneous polyethylene glycol concentration in said third suspension, at least a portion of the portion of said second suspension, incubated according to step (3), with a fourth aqueous solution, which has a volume between about 5 and about 10 times, preferably about 7, the volume of the portion of said incubated second suspension with which the fourth solution is mixed, said fourth solution consisting essentially of between about 20% (w/v) and about 50% (w/v), preferably 35%, polyethylene glycol of average molecular weight between about 3000 and about 5000 daltons, preferably 3350 daltons, in a solution with the same composition as said second solution;

(5) incubating at least a portion of said third suspension made in step (4) at between about 27° C. and about 33° C. for at least about 10 minutes to about 60 minutes, preferably about 30 minutes; and (6) heat shocking at least a portion of the portion of said third suspension incubated according to step (5).

The methods of the invention are preferably applied with cells of the methylotrophic species *Pichia pastoris*. Further, the methods of the invention are preferably applied with an auxotrophic mutant strain of *Pichia pastoris* wherein the genetic basis of the mutation(s) is sufficiently well characterized and for which genes have been isolated which are capable, upon transformation into the mutant strain, of complementing the mutant phenotype of the strain and thereby providing transformants which are prototrophic for the phenotype corresponding to the auxotrophic mutation and can be selected on the basis of such prototrophy. A number of such auxotrophic mutant strains of *P. pastoris* are known in the art, including strain GS115, an histidine-requiring strain on account of a mutation in the HIS4 gene and strain PPF1, an histidine and arginine-requiring strain on account of mutations in the HIS4 and ARG4 genes.

Cultures of strains GS115 and PPF1 were deposited under the terms of the Budapest Treaty on the International Recognition of the Deposit of Microorganisms for Purposes of Patent Procedure on Aug. 31, 1984 and Oct. 22, 1985, respectively, at the Northern Regional Research Laboratory Culture Depository of the United States Department of Agriculture in Peoria, Ill., U.S.A. The deposits of the cultures of both of the strains were accepted by that Depository under the terms of that Treaty. The deposit of the culture of strain GS115 was assigned deposit number Y-15851. The deposit of the culture of strain PPF1 was assiged deposit number Y-18017. All restrictions on access by the public to samples of the deposits will be irrevocably removed upon or prior to issuance of a U.S. patent on the present application.

While the methods of the invention can be applied to make transformants that are selected using a dominant selectable marker, such as G418-resistance, provided by a heterologous gene on DNA transformed into the cells to be transformed, it has been found that the transformation efficiency (i.e., the number of transformants obtained per unit mass of desired DNA per cell employed in the second suspension) is much lower when selection employs a dominant selectable marker than when it is based on complementation of an auxotrophic mutation.

The transformation method of the instant invention can be employed with virtually any DNA which is desired to be, and capable of being, transformed into a cell of a methylotrophic species of *Pichia pastoris* to confer on said cell a desired phenotype, such as the ability to express a desired protein. As understood by those skilled in the art, such DNA usually contains from about 20 to about 0.5 kilobase pairs. In fact, usually such a desired DNA will be shorter than about 20 kilobase pairs and will include a gene which confers on transformants a phenotype by which they can be selected from untransformed cells as well as a gene which is capable of being expressed in the transformants to produce a protein which provides the desired phenotype of the transformed cells. A desired DNA to be transformed into cells in accordance with the invention can be a circular plasmid, capable of being maintained in transformants with stability at least sufficient to measurably confer the desired phenotype on transformants, or a linearized plasmid or other linear DNA capable of integrating into the genome of transformants, preferably at a preselected locus therein, such as, e.g., the locus of the major alcohol oxidase gene (AOX1 gene), and, as integrated DNA, conferring the desired phenotype on transformants. Examples of desired DNAs and methods of identifying transformants therewith are known in the art. It has been found that the efficiency of transformation with the transformation method of the invention is much higher with linearized plasmid DNAs than with circular DNAs.

Alkali metal salts for use in accordance with the invention are lithium chloride and lithium sulfate. Most preferred is lithium chloride.

Any salt which is capable of buffering the solutions and suspensions employed in accordance with the invention at a pH of about 7 to about 8, preferably about 7, and which is non-toxic to the cells to be transformed can be employed in accordance with the invention. The skilled are aware of many such salts. The preferred one is Tris-HCl, at a concentration between about 1 mM and about 100 mM. The solutions and suspensions used in the invention also preferably include "EDTA", by which is intended collectively all forms, completely protonated and anionic, of ethylene diamine tetraacetate, at a concentration between about 0.1 mM and 10 mM.

The polyethylene glycol employed in the transformation method of the invention preferably has an average molecular weight between about 3000 and about 4000 daltons, more preferably about 3350.

The carrier DNA which is employed in the transformation method of the invention, optionally in all transformations according to the method but necessarily when the concentration of desired DNA is less than 10 $\mu$g per ml of said first suspension (which is combined with the third solution to make the second suspension) is DNA which is foreign to Pichia, such as *E. coli* DNA, salmon sperm DNA, herring sperm DNA, or the like. The carrier DNA, as understood by those skilled in the art, is sheared by a process such as sonication or digestion with a restriction enzyme. While such DNA can have from about 15 to about 0.5 kilobase pairs, preferably the carrier DNA has an average size less than about 1 kilobase pair. A particularly preferred carrier DNA is *E. coli* DNA digested to completion with the restriction enzyme HaeIII.

The invention will now be illustrated in some detail in the following examples.

EXAMPLE I

Preparing Competent Cells for Transformation

A 50 ml culture of *Pichia pastoris* was grown in YPD (1% yeast extract, 2% peptone, 2% dextrose) at 30° C. with shaking and cells were harvested at log phase, i.e., at an $OD_{600}$ of about 1 (about $5 \times 10^7$ cells/ml). Cells harvested at log phase were more efficiently transformed by the method of the invention than those in late log or stationary phase (contrary to the observations of Ito et al. and Davidow et al, supra). Harvesting was accomplished by centrifugation of the culture at 5° C.-10° C. at $1500 \times g$ for 10 minutes; the supernatant was discarded.

The cell pellet from the harvesting was washed once by suspension in 10 ml of sterile water followed by centrifugation as in the previous paragraph. Again, the supernatant was discarded.

The pellet was then washed by being suspended in sterile TE buffer (10 mM Tris-HCl, pH 7.4, 1 mM EDTA,) followed by centrifugation at 5° C.-10° C. at $1500 \times g$ for 10 minutes. Again, the supernatant was discarded.

Then the cells were suspended in a volume of TE buffer supplemented with 0.1M LiCl to bring the cells to a concentration of about $1.5 \times 10^8$ cells/ml. This suspension was incubated at 30° C. for 1 hour in a shaking air incubator (200–250 rpm). Incubation periods shorter than 45 minutes have been found to reduce transformation efficiency 10 to 20-fold compared to periods of an hour or longer. Incubation periods up to 2 hours have been found to have no significant effect on transformation frequency compared to incubations for 1 hour.

After the incubation, the cells were competent for transformation and could be used immediately for transformation, could be stored overnight at 4° C. without significant loss of transformation efficiency, or could be stored for longer periods as follows:

To store the competent cells frozen, harvest the cells after the incubation described in the preceding paragraph by centrifugation at 5° C.-10° C. at 1500×g for 10 minutes and then discard the supernatant. Then resuspend the pellet in a volume to bring the concentration of cells to $1.5 \times 10^8$ cells/ml of a solution of TE buffer supplemented with 0.1M LiCl, made 15% (v/v) in dimethylsulfoxide. The resulting suspension was dispensed into sterile tubes in 0.5 ml aliquots and the tubes were then frozen on dry ice and stored at −70° C.

Frozen competent cells were prepared for transformation by removing a tube of cells from the freezer and thawing on ice. Then the thawed solution was centrifuged in a benchtop microfuge to pellet cells and the supernatant was discarded. Then the pellet was washed by suspension, in a volume to bring the concentration of cells to $1.5 \times 10^8$ cells/ml, of a solution, of TE buffer supplemented with 0.1 M LiCl, followed by centrifugation at 5° C.-10° C. at 1500×g for 10 minutes and discarding of the supernatant. The pellet was then resuspended in a volume to bring the concentration of cells to $1.5 \times 10^8$ cells/ml, of TE buffer supplemented with 0.1M of LiCl.

Competent cells, frozen and thawed and prepared for transformation as described in this example, have about a five-fold reduction in transformation efficiency independently of the length of the storage.

Those skilled in the art will understand that the various washing steps described in this example, while consistent with good microbiological practice and possibly helpful in maintaining transformation efficiency of competent cells, are not required to make the cells competent. The step required to make the cells competent is the incubation for at least 45 minutes at a temperature in the range of 27° C.-33° C., preferably 30° C., of the suspension of the cells in TE buffer supplemented with LiCl.

The pH of the TE buffered solutions described in these examples is preferably about 7.4 but can range between about 7.0 and 7.8 without significant adverse effects on transformation efficiency or otherwise.

EXAMPLE II

Transformation of Cells

To a sterile, 12×75 mm polypropylene tube were added: 10 μg HaeIII-digested *E. coli* DNA as carrier DNA and 1 ng-20 μg of the desired DNA (preferably linearized plasmid DNA with termini to direct the DNA to integration at a preselected locus of the transformed strain's genome) in less than 20 μl of TE buffer, and 100 μl of competent cells (about $1.5 \times 10^7$ cells) in TE buffer supplemented with 0.1M LiCl. The mixture was then incubated at 30° C. (27° C.-33° C.) for 30 minutes (10 minutes to an hour). After the incubation, 0.7 ml of a solution, of TE buffer supplemented with 0.1M LiCl, made 40% with polyethylene glycol of average molecular weight of 3350 daltons ("PEG$_{3350}$") was added to the incubation mixture and the resulting suspension was vortexed briefly to disperse the PEG homogeneously. The PEG-containing suspension was then incubated at 30° C. for 30 minutes in a stationary water bath. Finally the suspension was heat shocked by immersion at 37° C. (35° C.-39° C.) for 5 minutes (2 minutes 10 minutes) in a stationary water bath, followed in turn with discarding of the supernatant. Finally, prior to screening for transformants, the pellet was resuspended in 0.1 ml of sterile water.

Screening for transformants can be carried out by spreading the final suspension of cells in water on a selective plate (e.g., in the case of *P. pastoris* strain GS115 transformed with a desired DNA that complements the HIS4 mutation, agar with 0.67% yeast nitrogen base, without amino acids, plus 2% glucose), incubating the plate for 3 days at 30° C. and then identifying transformants by the growth of colonies on the plate.

Transformed colonies can be recovered for further analysis or for use by adding sterile water to the plate and then scraping colonies off the agar surface and removing them to tubes.

EXAMPLE III

Using the procedure of Example II cells of *Pichia pastoris* GS115 and *Pichia pastoris* PPF1 were transformed with the variations as noted with plasmid designated pYJ30 (NRRL No. B-15890 pYJ30 in *E. coli*) either uncut or cut with StuI. The cells were used immediately after being made competent via the manner of Example I. The following transformation efficiencies were obtained.

| Host | OD$_{600}$[1] | Desired DNA[2] | Salt[3] | No. of Transformants |
|---|---|---|---|---|
| GS115 | 1 | A[3] | 0.1 M LiCl | 3689 |
| PPF1 | 0.925 | A | 0.1 M LiCl | 229 |
| GS115 | 1.23 | A | 0.1 M LiCl | 2056 |
| GS115 | 1.23 | B | 0.1 M LiCl | 601 |
| GS115 | 1.23 | A | 0.1 M Li(OAc) | 164 |
| GS115 | 1.23 | B | 0.1 M Li(OAc) | 16 |
| GS115 | 1.23 | A | 0.1 M Li$_2$SO$_4$ | 2400 |
| GS115 | 1.23 | B | 0.1 M Li$_2$SO$_4$ | 215 |
| GS115 | 0.27 | A | 0.1 M LiCl | 3100 |
| GS115 | 0.54 | A | 0.1 M LiCl | 1560 |
| GS115 | 1.05 | A | 0.1 M LiCl | 1589 |
| GS115 | 2.25 | A | 0.1 M LiCl | 590 |
| GS115 | 1.25 | A | 0.05 M LiCl | 4994 |
| GS115 | 1.25 | A | 0.1 M LiCl | 5108 |
| GS115 | 1.25 | A | 0.25 M LiCl | 3666 |
| GS115 | 1.25 | A | 0.5 M LiCl | 563 |
| GS115 | 1.25 | A | 0.75 M LiCl | 1 |
| GS115 | 1.25 | A | 1.0 M LiCl | 3 |

[1] The OD of the culture at the time cells were harvested for the transformation procedure
[2] "A" means StuI-cut pYJ30. "B" means circular, uncut pYJ30.
[3] The same salt, at the same concentration, was used in all solutions employed in the transformation process.

While the invention has been described with some specificity in the present application, persons skilled in the art will recognize many modifications and variations that are within the spirit of the invention. Such modifications and variations are intended to be within the scope of the invention as described and claimed herein.

We claim:

1. A method for making whole cells of *Pichia pastoris* competent for transformation which comprises maintaining said cells in suspension for a period of from 45 to 120 minutes at a cell concentration in the range of $5 \times 10^7$ to $5 \times 10^8$ per ml in an aqueous solution of a non-toxic salt of an alkali metal selected from LiCl and Li$_2$SO$_4$ at a concentration of between 50 mM and about 500 mM, said solution being maintained at a temperature in the range of about 27° C.-33° C. and buffered at a pH in the range of about 7 to about 8.

2. A method according to claim 1 wherein said aqueous solution is buffered with Tris-HCl at a concentration between about 1 mM and about 100 mM and comprises EDTA at a concentration between about 0.1 mM and about 10 mM and has pH of 7.4.

3. A method according to claim 1 wherein said *Pichia pastoris* is GS115 (NRRL Y-15851).

4. A method according to claim 1 wherein said *Pichia pastoris* is PPF1 (NRRL Y-18017).

5. A method for transforming whole cells of *Pichia pastoris* with a desired DNA, which method comprises:
  (1) providing a first suspension of from $5 \times 10^7$ to $5 \times 10^8$ competent cells/ml in an aqueous solution having a concentration between about 50 mM and about 500 mM of a non-toxic alkali metal salt selected from LiCl and Li$_2$SO$_4$ and buffered to a pH between about 6 and about 8;
  (2) making a second suspension of competent cells by combining (a) said first suspension of said competent cells in an aqueous solution comprising the same alkali metal salt as used in step (1) and (b) a third aqueous solution with a volume less than $0.2\times$ that of said suspension, said third aqueous solution being buffered at a pH between about 7 and about 8 and comprising between about 1 μg and about 20 μg of desired DNA per ml of said first suspension combined with said third solution;
  (3) incubating at least a portion of said second suspension made in step (2) at a temperature between about 27° C. and about 33° C. for a period between about 10 minutes to 60 minutes;
  (4) making a third suspension of said cells by mixing, to establish substantially homogenous polyethylene glycol concentration in said third suspension, at least a portion of the portion of said second suspension, incubated according to step (3), with a fourth aqueous solution, which has a volume between about 5 and about 10 times the volume of the portion of said incubated second suspension with which the fourth solution is mixed, said fourth solution consisting essentially of between about 20% (w/v) and about 50% (w/v) polyethylene glycol of average molecular weight between about 3000 and about 5000 daltons in a solution with the same composition as said second solution;
  (5) incubating at least a portion of said third suspension made in step (4) at between about 27° C. and about 33° C. for at least about 10 minutes to about 60 minutes; and
  (6) heat shocking at least a portion of the portion of said third suspension incubated according to step (5).

6. A process according to claim 5 wherein said cells have been made competent by a method comprising maintaining said cells in suspension for at least about 45 minutes to about 120 minutes at a concentration between about $5 \times 10^7$ and about $5 \times 10^8$ cells/ml in a first aqueous solution of lithium chloride or lithium sulfate at a concentration between about 50 mM and about 500 mM, said first solution maintained at a temperature between about 27° C. and about 33° C. and buffered to a pH between about 6 and about 8.

7. A method according to claim 5 wherein each of said second and said third solutions is buffered with Tris-HCl at a concentration between about 1 mM and about 100 mM, comprises EDTA at a concentration between about 0.1 mM and about 10 mM, and has a pH between about 7.0 and about 7.8.

8. A method according to claim 7 wherein the concentration of cells in said first suspension is between about $1.0 \times 10^8$ and about $2.5 \times 10^8$ cells/ml, wherein the amount of desired DNA in said third solution is between about 1 ng and about 20 μg per ml of said first suspension, wherein said third solution comprises about 10 μg of carrier DNA, and wherein the heat shocking consists essentially of incubating a portion of said third suspension incubated according to step (5) at a temperature between about 35° C. and about 39° C. for between about 2 minutes and about 10 minutes followed by reducing the temperature of said heat shocked portion to below about 33° C.

9. A method according to claim 7 wherein the cells of *Pichia pastoris* are of a strain which has an auxotrophic mutation, wherein the desired DNA is a linear DNA which is capable of integration at a preselected locus in the *Pichia pastoris* genome and which comprises a gene for a selectable marker which complements said auxotrophic mutation, and wherein, after the heat shocking step, transformants are selected on the basis of prototrophy for the phenotype due to said auxotrophic mutation.

10. A method according to claim 8 wherein the cells of *Pichia pastoris* are of a strain which has an auxotrophic mutation, wherein the desired DNA is a linear DNA which is capable of integration at a preselected locus in the *Pichia pastoris* genome and which comprises a gene for a selectable marker which complements said auxotrophic mutation, and wherein, after the heat shocking step, transformants are selected on the basis of prototrophy for the phenotype due to said auxotrophic mutation.

11. A method according to claim 5 wherein the cells are of *Pichia pastoris* strain GS115.

12. A method according to claim 7 wherein the cells are of *Pichia pastoris* strain GS115.

13. A method according to claim 8 wherein the cells are of *Pichia pastoris* strain GS115.

14. A method according to claim 9 wherein the cells are of *Pichia pastoris* strain GS115.

15. A method according to claim 10 wherein the cells are of *Pichia pastoris* strain GS115.

16. A method according to claim 1 wherein the cells are of *Pichia pastoris* strain PPF1.

17. A method according to claim 5 wherein the cells are of *Pichia pastoris* strain PPF1.

18. A method according to claim 7 wherein the cells are of *Pichia pastoris* strain PPF1.

19. A method according to claim 8 wherein the cells are of *Pichia pastoris* strain PPF1.

20. A method according to claim 9 wherein the cells are of *Pichia pastoris* strain PPF1.

21. A method according to claim 10 wherein the cells are of *Pichia pastoris* strain PPF1.

22. A method according to claim 5 wherein when the amount of desired DNA is less than about 10 μg per ml of said first suspension combined with said third solution, said third solution comprises a mass of carrier DNA of 10 μg and further that the amount of said carrier DNA does not exceed 50 μg per ml of said first suspension combined with said third solution.

23. A method according to claim 22 wherein said carrier DNA does not exceed 50 μg per ml of said first suspension combined with said solution.

* * * * *